US010900978B2

(12) United States Patent
Bergmann et al.

(10) Patent No.: US 10,900,978 B2
(45) Date of Patent: Jan. 26, 2021

(54) METHOD FOR PREDICTING THE RISK OF OBESITY IN A SUBJECT

(71) Applicant: SPHINGOTEC GMBH, Hennigsdorf (DE)

(72) Inventors: Andreas Bergmann, Berlin (DE); Olle Melander, Limhamn (SE)

(73) Assignee: SPHINGOTEC GMBH, Hennigsdorf (DE)

( * ) Notice: Subject to any disclaimer, the term of this patent is extended or adjusted under 35 U.S.C. 154(b) by 11 days.

(21) Appl. No.: 15/553,839

(22) PCT Filed: Feb. 26, 2016

(86) PCT No.: PCT/EP2016/054106
§ 371 (c)(1),
(2) Date: Aug. 25, 2017

(87) PCT Pub. No.: WO2016/066862
PCT Pub. Date: May 6, 2016

(65) Prior Publication Data
US 2018/0246127 A1 Aug. 30, 2018

(30) Foreign Application Priority Data

Feb. 27, 2015 (EP) ..................................... 15156995
Apr. 23, 2015 (EP) ..................................... 15164910

(51) Int. Cl.
*G01N 33/74* (2006.01)
*G01N 33/68* (2006.01)
*G01N 33/48* (2006.01)

(52) U.S. Cl.
CPC ............. *G01N 33/74* (2013.01); *G01N 33/48* (2013.01); *G01N 33/68* (2013.01); *G01N 2333/4706* (2013.01); *G01N 2800/044* (2013.01); *G01N 2800/50* (2013.01)

(58) Field of Classification Search
CPC ........ G01N 33/48; G01N 33/49; G01N 33/68; G01N 33/74; G01N 2333/4706; G01N 2800/044; G01N 2800/50
USPC .............................................. 436/63, 86, 89
See application file for complete search history.

(56) References Cited

U.S. PATENT DOCUMENTS

| | | | |
|---|---|---|---|
| 10,473,670 B2 * | 11/2019 | Evers ................... | A61K 31/713 |
| 2011/0097757 A1 | 4/2011 | Hancock et al. | |
| 2015/0031144 A1 * | 1/2015 | Bergmann .......... | G01N 33/574 436/510 |
| 2015/0056203 A1 | 2/2015 | Bergmann et al. | |
| 2015/0118236 A1 * | 4/2015 | Bergmann ............. | G01N 33/74 424/139.1 |
| 2016/0097781 A1 * | 4/2016 | Bergmann ............. | G01N 33/74 436/501 |
| 2017/0248610 A1 * | 8/2017 | Evers .................. | G01N 33/6893 |

FOREIGN PATENT DOCUMENTS

| | | |
|---|---|---|
| WO | 2009006568 A1 | 4/2011 |
| WO | 2013132090 A1 | 9/2013 |

OTHER PUBLICATIONS

Ernst et al. Peptides, vol. 27, Mar. 7, 2006, pp. 1787-1793.*
International Search Report for PCT/EP2016/054106 dated Jun. 8, 2016.
Reilly, J. J. et al., "Obesity: diagnosis, prevention, and treatment; evidence based answers to common questions," Archives of Disease in Childhood, Jun. 1, 2002, vol. 86, No. 6, pp. 392-394.
Kyrgios, I. et al., "Elevated circulating levels of the serum acute-phase protein YKL-40 (chitinase 3-like protein 1) are a marker of obesity and insulin resistance in prepubertal children," Metabolism, Clinical and Experimental, Jun. 1, 2002, vol. 61, No. 4, pp. 562-568.
"What is Metabolic Syndrome?" 2012, pp. 1-2, Oct. 21, 2015.
Wisen, O. et al., "Plasma concentrations of regulatory peptides in obseity following modified sham feeding (MSF) and a liquid test meal," Regulatory Peptides, 1992, vol. 39, No. 1, pp. 43-54.
Holdstock, C. et al., "Postprandial changes in gut regulatory peptides in gastric bypass patients," International Journal of Obesity, 2008, vol. 32, No. 11, pp. 1640-1646.
Rovere, C. et al., "Impaired processing of brain proneurotensin and promelanin-concentrating hormone in obese fat/ fat mice," Endocrinology, 1996, vol. 137, No. 7, pp. 2954-2958.
Christ-Crain, M. et al., "Effect of Gastric Bypass and Gastric Banding on Proneurotensin Levels in Morbidly Obese Patients," Journal of Clinical Endocrinology & Metabolism, 2006, vol. 91, No. 9, pp. 3544-3547.
Service, F. J. et al., "Neurotensin in diabetes and obesity," Regulatory Peptides, 1986, vol. 14, No. 1, pp. 85-92.

(Continued)

*Primary Examiner* — Maureen Wallenhorst
(74) *Attorney, Agent, or Firm* — Millen White Zelano & Branigan, PC; Brion P. Heaney

(57) ABSTRACT

Subject matter of the present invention is a method for determining the fat processing activity and/or predicting the risk of obesity in a subject. The method involves determining the level of pro-neurotensin or fragments thereof of at least 5 amino acids in a bodily fluid obtained from a subject; and correlating the determined level of pro-neurotensin or fragments thereof with fat processing activity and/or the risk of incidence of obesity in the subject, wherein an elevated level is indicative of enhanced fat processing activity and/or predictive for an enhanced risk of getting obesity.

20 Claims, 2 Drawing Sheets

Specification includes a Sequence Listing.

(56) References Cited

OTHER PUBLICATIONS

Williams, G. et al., "Reduced hypothalamic neurotensin concentrations in the genetically obese diabetic (ob/ob) mouse: Possible relationship to obesity," Clinical and Experimental Metabolism, 1991, vol. 40, No. 10, pp. 1112-1116.

* cited by examiner

METHOD FOR PREDICTING THE RISK OF OBESITY IN A SUBJECT

Subject matter of the present invention is a method for determining the fat processing activity and/or for predicting the risk of obesity in a subject comprising the following steps:
- determining by an immunoassay the level of pro-neurotensin 1-117 or fragments thereof of at least 5 amino acids or pro-neurotensin 1-117 comprising peptides in a bodily fluid obtained from said subject or
- determining the level of pro-neurotensin 1-117 or fragments thereof of at least 5 amino acid in a bodily fluid obtained from said subject; and
- correlating said level of pro-neurotensin 1-117 or fragments thereof or pro-neurotensin 1-117 comprising peptides with the fat processing activity and/or the a risk of incidence of obesity in said subject, wherein an elevated level is indicative of an enhanced fat processing activity and/or predictive for an enhanced risk of obesity and wherein subject is not obese at the time the sample of bodily fluid is taken from said subject.

Neurotensin is a 13-amino acid neuropeptide derived from the prepro-neurotensin precursor and stochiometrically released together with the stable 117-amino acid peptide pro-neurotensin (P-NT) and the mature hormone binds to three different receptors, neurotensin receptor 1 and 2 (Ntsr1 and Ntsr2), which are G-protein coupled receptors and neurotensin receptor 3 (Ntsr3) which is non-G-protein coupled and also known as Sortillin-1 (SORT1).

Neurotensin is released peripherally from the small intestine as well as centrally from the hypothalamus. The peripheral secretion of neurotensin is stimulated by food-intake, especially by fat, and is known to regulate gastrointestinal motility and pancreatic and biliary secretion. Interestingly, neurotensin is implicated in appetite control as an anorectic hormone as it acutely reduces food intake following both central (intracerebroventricular) and peripheral (intraperitoneal) injection in rats, an effect which seems mainly mediated through the neurotensin-1 receptor (Ntsr1). In obese as compared to normal-weight human subjects, postprandial plasma neurotensin concentration was reduced following a liquid fatty meal (Wisen et al. 1992, Reg Peptides 39(1): 43-54) and lower fasting neurotensin levels have been observed in obese human subjects compared with lean controls (Weiss et al. 2001, Obes Surg 11: 735-739), suggesting that the regulation of neurotensin secretion is disturbed in obesity. However, no large study has investigated if and how neurotensin is related to the risk of developing obesity.

A subject of the present invention was to investigate the prognostic power of NT for predicting the risk of obesity in a non-obese subject. To address this issue, we measured stable fragments of pro-neurotensin in fasting plasma in said Swedish prospective cohort study (Malmö Diet and Cancer Study) and related baseline level of this biomarker to obesity during 15 years of follow-up.

The risk of obesity in a non-obese subject may correlate to the fat processing activity of said subject. Thus, the determination of levels of pro-neurotensin 1-117 or fragments thereof of at least 5 amino acids or pro-neurotensin 1-117 comprising peptides in a bodily fluid may be a determination of the fat processing activity.

Subject matter of the present invention is a method for determining the fat processing activity and/or for predicting the risk of obesity in a subject comprising the following steps:
- determining by an immunoassay the level of pro-neurotensin 1-117 or fragments thereof of at least 5 amino acids or pro-neurotensin 1-117 comprising peptides in a bodily fluid obtained from said subject or
- determining the level of pro-neurotensin 1-117 or fragments thereof of at least 5 amino acid in a bodily fluid obtained from said subject; and
- correlating said level of pro-neurotensin 1-117 or fragments thereof or pro-neurotensin 1-117 comprising peptides with the fat processing activity and/or the a risk of incidence of obesity in said subject, wherein an elevated level is indicative of an enhanced fat processing activity and/or predictive for an enhanced risk of obesity and wherein subject is not obese at the time the sample of bodily fluid is taken from said subject.

Fat processing activity is defined as absorption, metabolism and/or storage of fat in the human body. Fat processing activity is synonymous to fat up-take by the body or to the capability to storage fat that is up-taken and converted. Woman with higher fat processing activity are at higher risk of getting obese.

Dietary fat consists of a variety of polar and nonpolar lipids. Triacylglycerol (TAG) is the dominant fat in the diet, contributing 90-95% of the total energy derived from dietary fat. Dietary fats also include phospholipids, sterols (e.g., cholesterol), and many other lipids (e.g., fat-soluble vitamins). The digestion of lipids begins in the oral cavity through exposure to lingual lipases, which are secreted by glands in the tongue to begin the process of digesting triglycerides. Digestion continues in the stomach through the effects of both lingual and gastric enzymes. The stomach is also the major site for the emulsification of dietary fat and fat-soluble vitamins, with peristalsis a major contributing factor. Crude emulsions of lipids enter the duodenum as fine lipid droplets and then mix with bile and pancreatic juice to undergo marked changes in chemical and physical form. Emulsification continues in the duodenum along with hydrolysis and micellization in preparation for absorption across the intestinal wall. Bile and pancreatic juice provide pancreatic lipase, bile salts, and colipase, which function cooperatively to ensure the efficiency of lipid digestion and absorption. TAG is digested primarily by pancreatic lipase in the upper segment of the jejunum. Free fatty acids are taken up from the intestinal lumen into the enterocytes and used for the biosynthesis of neutral fats. Once inside the enterocyte, the products of TAG hydrolysis must traverse the cytoplasm to reach the endoplasmic reticulum (ER), where they are used to synthesize complex lipids.

The major lipoproteins secreted by the intestine are VLDL and chylomicrons. Of these, the chylomicrons are synthesized exclusively in the intestine to transport dietary fat and fat-soluble vitamins into the blood. Chylomicrons are primarily very large, spherical TAG-rich particles that also contain PLs, cholesterol, vitamin E, vitamin A, and protein. The lipoprotein core contains TAG, cholesteryl esters, and fat-soluble vitamins, whereas the surface contains a monolayer of phospholipids (mainly phosphatidylcholine), free cholesterol, and protein.

As they circulate, the triacylglycerols of chylomicrons undergo hydrolysis by lipoprotein lipase, an enzyme located on the surface of capillary endothelial cells of muscle and adipose tissues. Circulating chylomicrons have a half-life of 5-10 minutes. The hydrolysis of chylomicrons leads to release of fatty acids and glycerol from the core of chylomicrons, as well as unesterified cholesterol from the surface coat of these particles. The delipidation occurs predominantly in the adipose, muscle and heart tissues which take up and oxidize or store the fatty acids released by lipoprotein lipase.

Fatty acids, cholesterol and bile acids that escape intestinal absorption are excreted as fecal fatty acids, as well as neutral and acidic sterols, respectively.

In subjects with an effective fat processing activity the proportion of fat absorbed by the gastrointestinal tract is lower, the amount of fat absorbed is metabolized nearly completely and no or only a small amount of fat is transported and stored in the adipocytes of the subjects. In contrast, in subjects with an inefficient fat processing activity the proportion of fat absorption by the GI tract is high, but the fat absorbed is metabolized to a smaller extent and more fat is transported and stored in the adipocytes of the subject.

The term "subject" as used herein refers to a living human or non-human organism. Preferably herein the subject is a human subject. In a specific embodiment of the invention said subject is a non-diabetic subject. In another specific embodiment of the invention said subject is non-IFG (non-pre-diabetic) subject. In another specific embodiment of the invention the subject does not suffer from the metabolic syndrome. In another specific embodiment of the invention the subject does not suffer from a cardiac disease. In another specific embodiment of the invention the subject does not suffer from cancer. In another specific embodiment of the invention the subject is a female subject.

The term "cardiac disease" includes myocardial infarction, ischemic heart disease, stroke, heart failure (acute or chronic heart failure), atrial fibrillation and atrial flutter.

The term "risk of new-onset obesity" is synonymously to "risk of obesity" wherein subject is not obese at the time the sample of bodily fluid is taken from said subject.

In one embodiment of the invention the level of pro-neurotensin or fragments thereof of at least 5 amino acids or pro-neurotensin 1-117 comprising peptides in a bodily fluid is the fasting level of pro-neurotensin or fragments thereof of at least 5 amino acid or pro-neurotensin 1-117 comprising peptides. Fasting level means no food uptake 10 hours or preferably 12 hours prior blood sampling.

As the fasting level of pro-neurotensin or fragments thereof of at least 5 amino acid or pro-neurotensin 1-117 comprising peptides is not triggered by recent fat up-take it seems that in one embodiment the fasting level is a measure to quantify the fat processing activity of said subject. This may be a missing link that explains why some subjects are susceptible to become obese as they process high quantities of up-taken fat whereas other individuals with low levels of pro-neurotensin or fragments thereof of at least 5 amino acid or pro-neurotensin 1-117 comprising peptides have a low level of fat processing activity. But also determination of pro-neurotensin or fragments thereof of at least 5 amino acid or pro-neurotensin 1-117 comprising peptides in non-fasting sample may be an indicator of fat-processing activity as some subjects may have higher enhancements of levels than others triggered by the same amount of fat up taken. In the latter setting pro-neurotensin or fragments thereof of at least 5 amino acid or pro-neurotensin 1-117 comprising peptides may be measured at baseline before fat-uptake and thereafter, whereas subjects with enhanced fat processing activity will react with higher amounts of released pro-neurotensin or fragments thereof of at least 5 amino acid or pro-neurotensin 1-117 comprising peptides upon fat-uptake.

Thus, one embodiment of the invention is a method for determining the fat processing activity and/or for predicting the risk of obesity in a subject comprising the following steps:
  determining by an immunoassay the level of pro-neurotensin 1-117 or fragments thereof of at least 5 amino acids or pro-neurotensin 1-117 comprising peptides in a non-fasting or fasting sample of bodily fluid obtained from said subject or
  determining the level of pro-neurotensin 1-117 or fragments thereof of at least 5 amino acid in non-fasting or fasting sample of a bodily fluid obtained from said subject; and
  administering to said subject fat
  determining by an immunoassay the level of pro-neurotensin 1-117 or fragments thereof of at least 5 amino acids or pro-neurotensin 1-117 comprising peptides in a sample of bodily fluid obtained from said subject after fat-uptake or
  determining the level of pro-neurotensin 1-117 or fragments thereof of at least 5 amino acid in of a bodily fluid obtained from said subject after fat-uptake; and
  calculating the difference between said levels after and before fat-uptake and
  correlating said difference between said levels after and before fat-uptake of pro-neurotensin 1-117 or fragments thereof or pro-neurotensin 1-117 comprising peptides with the fat processing activity and/or the a risk of incidence of obesity in said subject, wherein a higher difference is indicative of an enhanced fat processing activity and/or predictive for an enhanced risk of obesity
  and wherein the subject is not obese at the time the sample of bodily fluid is taken from said subject.

This means that the difference between the level of pro-neurotensin 1-117 or fragments thereof of at least 5 amino acids or pro-neurotensin 1-117 comprising peptides before fat up-take and said level after fat up-take may be indicative of the fat processing activity. The status of said subject before fat up-take may be fasting or non-fasting. A standardized amount of fat is administered to said subjects (oral fat tolerance test), e.g. a specific amount of cream containing a specific amount of fat. It has been shown in Example 4 that some individuals react more sensitive to fat-uptake than others and thus, have a higher fat processing activity.

The level of pro-neurotensin 1-117 or fragments thereof of at least 5 amino acids or pro-neurotensin 1-117 comprising peptides in a bodily fluid obtained from said subject that is predictive for the risk of developing new-onset obesity and is indicative for fat processing activity is released from the small intestine. The release of neurotensin from the small intestine is stimulated by food intake, especially by fat (Go and Demol 1981. Peptides (Suppl. 2): 267-269), and is known to regulate gastrointestinal motility and pancreatic and biliary secretion (Reinecke 1985. Prog Histochem Cytochem 16: 1-172). Pro-neurotensin 1-117 and fragments thereof or pro-neurotensin 1-117 comprising peptides are used as a surrogate marker for the released neurotensin as neurotensin and pro-neurotensin 1-117 and fragments thereof or pro-neurotensin 1-117 comprising peptides are released in equimolar amounts from pro-neurotensin.

It is the surprising finding of the present invention that the peripheral secretion of neurotensin/pro-neurotensin 1-117 or fragments thereof of at least 5 amino acids or pro-neurotensin 1-117 comprising peptides is indicative for the susceptibility of a subject for developing new-onset obesity and is a measure of fat processing activity. Thus, dietary measures as reduction of fat uptake may lower said risk in said subject.

The correlation between the level of pro-neurotensin or fragments thereof of at least 5 amino acids or PNT 1-117 comprising peptides in a bodily fluid obtained from said subject and the risk of developing obesity and also the fat processing activity is continuous, i.e. the higher the level the higher the risk.

For the sake of practicability the person skilled in the art may use threshold(s).

The term "elevated level" means a level above a certain threshold level.

Threshold levels may be determined by measuring samples from subjects who did develop a certain condition (e.g. obesity) and samples from subjects who did not develop the condition. One possibility to determine a threshold is the calculation of receiver operating characteristic curves (ROC curves), plotting the value of a variable versus its relative frequency in the "normal" population (e.g. subjects who did not develop the condition of obesity) and "disease" population (e.g. subjects who did develop the condition of obesity). A distribution of the marker levels for subjects developing or not developing a certain condition will likely overlap. Under such conditions, a test does not absolutely distinguish "normal" from "disease" with 100% accuracy, and the area of overlap indicates where the test cannot distinguish normal from "disease". A threshold is selected, above which (or below which, depending on how a marker changes with the "disease") the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (Hanley et al. 1982. *Radiology* 143: 29-36). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement. The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test. The odds ratio is a measure of effect size, describing the strength of association or non-independence between two binary data values (e.g. the ratio of the odds of an event occurring in test negative group to the odds of it occurring in the test positive group).

Threshold levels can be obtained for instance from a Kaplan-Meier analysis, where the occurrence of a disease or the probability of a serious condition and/or death is correlated with the e.g. quartiles of the respective markers in the population. According to this analysis, subjects with marker levels above the 75th percentile have a significantly increased risk for getting the diseases according to the invention. This result is further supported by Cox regression analysis with adjustment for classical risk factors. The highest quartile versus all other subjects is highly significantly associated with increased risk for getting a disease or the probability of a serious condition and/or death according to the invention.

Other preferred cut-off values are for instance the 90th, 95th or 99th percentile of a reference population. By using a higher percentile than the 75th percentile, one reduces the number of false positive subjects identified, but one might miss to identify subjects, who are at moderate, albeit still increased risk. Thus, one might adapt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

Other mathematical possibilities to calculate an individual's risk by using the individual's marker level value and other prognostic laboratory and clinical parameters are for instance the NRI (Net Reclassification Index) or the IDI (Integrated Discrimination Index). The indices can be calculated according to Pencina (Pencina M J, et al.: Evaluating the added predictive ability of a new marker: from area under the ROC curve to reclassification and beyond. Stat Med. 2008; 27:157-172).

A bodily fluid may be selected from the group comprising blood, serum, plasma, urine, cerebrospinal fluid (CSF), and saliva. In one specific embodiment a bodily fluid may be selected from the group comprising blood, serum, plasma.

The present data suggest a strong correlation between the level of pro-neurotensin or fragments thereof, especially pro-neurotensin 1-117 or fragments thereof or pro-neurotensin 1-117 comprising peptides with the development of new-onset obesity and with the fat processing activity.

Fragments of pro-neurotensin that may be determined in a bodily fluid may be e.g.

```
(Pro-neurotensin 1-147)
                                         SEQ ID NO: 1
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVIKRK

IPYILKRQLY ENKPRRPYIL KRDSYYY (pro-neurotensin 1-125 (large neuromedin N))
                                         SEQ ID NO: 2
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVI KR

KIPYIL

SEQ ID NO: 3 (neuromedin N:)

(neurotensin)
                                         SEQ ID NO: 4
pyroQLYENKPRRP YIL
```

-continued (pro-neurotensin 1-117)
SEQ ID NO: 5
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVI (pro-neurotensin 1-132)
SEQ ID NO: 6
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVIKRK

IPYILKRQLY EN

SEQ ID No 7:
(Pro-Neurotensin 1-140 (large neurotensin)
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVIKRK

IPYILKRQLY ENKPRRPYIL (pro-neurotensin 120-140)
SEQ ID NO: 8
KIPYILKRQL YENKPRRPYI L (pro-neurotensin 120-147)
SEQ ID NO: 9
KIPYILKRQL YENKPRRPYIL KRDSYYY (pro-neurotensin 128-147)
SEQ ID NO: 10
QLYENKPRRP YILKRDSYYY In a more specific embodiment of the method according to the present invention the level of pro-neurotensin 1-117 is determined.

In a specific embodiment the level of pro-neurotensin, especially pro-neurotensin 1-117 or fragments thereof or pro-neurotensin 1-117 comprising peptides, is measured with an immunoassay. More specifically an immunoassay is used as described in Ernst et al. Peptides 27 (2006) 1787-1793. In one specific embodiment the immune reactivity of pro-neurotensin 1-117 is determined wherein immune reactivity means the following:

Determining the level of pro-neurotensin or fragments thereof may mean that the immunoreactivity towards pro-neurotensin or fragments thereof including neurotensin and neuromedin N is determined. A binder used for determination of pro-neurotensin or fragments thereof including neurotensin and neuromedin N depending of the region of binding may bind to more than one of the above displayed molecules. This is clear to a person skilled in the art.

Thus, according to the present invention the level of immunoreactive analyte by using at least one binder that binds to a region within the amino acid sequence of any of the above peptide and peptide fragments, (i.e. pro-neurotensin (pro-NT) and fragments according to any of the sequences 1 to 10), is determined in a bodily fluid obtained from said subject; and correlated to the specific embodiments of clinical relevance.

In a more specific embodiment of the method according to the present invention the level of pro-NT 1-117 is determined (SEQ ID NO. 5: pro-neurotensin 1-117). In a more specific embodiment the level of immunoreactive analyte by using at least one binder that binds to pro-NT 1-117 is determined and is correlated to the specific embodiments of clinical relevance according to the invention.

In another embodiment of the invention the immunoreactivity towards pro-neurotensin or fragments thereof not including neurotensin and neuromedin N is determined.

An immunoassay that may be useful for determining the level of pro-neurotensin or fragments thereof of at least 5 amino acids or pro-neurotensin 1-117 comprising peptide may comprise the steps at outlines in example 2. An immunoassay that may be useful for determining the level of pro-neurotensin or fragments thereof of at least 5 amino acids or pro-neurotensin 1-117 comprising peptide may comprise at least one antibody or at least two antibodies directed against an epitope within pro-neurotensin 1-117. At least of these antibodies may be labelled. All thresholds and values have to be seen in light of the test and the calibration used according to Example 2. A person skilled in the art may know that the absolute value of a threshold might be influenced by the calibration used. This means that all values and thresholds given herein are to be understood in context of the calibration used in herein (Example 2). A human pro-NT-calibrator is available by ICI-Diagnostics, Berlin, Germany. Alternatively, the assay may be calibrated by synthetic or recombinant pro-NT 1-117 or fragments thereof (see also Ernst et. al, 2006).

In one embodiment of the invention it may be a so-called POC-test (point-of-care), that is a test technology which allows performing the test within less than 1 hour near the patient without the requirement of a fully automated assay system. One example for this technology is the immunochromatographic test technology.

In one embodiment of the invention such an assay is a sandwich immunoassay using any kind of detection technology including but not restricted to enzyme label, chemiluminescence label, electrochemiluminescence label, preferably a fully automated assay. In one embodiment of the invention such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, Biomerieux Vidas®, Alere Triage®.

A variety of immunoassays are known and may be used for the assays and methods of the present invention, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), dipstick immunoassays and immuno-chromatography assays.

In one embodiment of the invention at least one of said two binders is labeled in order to be detected.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

In a preferred embodiment said label is selected from the group comprising chemiluminescent label, enzyme label, fluorescence label, radioiodine label.

The assays can be homogenous or heterogeneous assays, competitive and non-competitive assays. In one embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person.

In another embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

In another embodiment, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, auch as CY3, CY5, CY3.5, CY5.5, Cy7, Xanthen, 6-Carboxy-2',4', 7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in (24). Preferred chemiluminescent dyes are acridiniumesters.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ M$^{-1}$.

In the context of the present invention, "binder molecules" are molecules which may be used to bind target molecules or molecules of interest, i.e. analytes (i.e. in the context of the present invention pro-Neurotensin and fragments thereof), from a sample. Binder molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, binder molecules may for instance be selected from the group comprising a nucleic acid molecule, a carbohydrate molecule, a PNA molecule, a protein, an antibody, a peptide or a glycoprotein. Preferably, the binder molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

Chemiluminescent label may be acridinium ester label, steroid labels involving isoluminol labels and the like.

Enzyme labels may be lactate dehydrogenase (LDH), creatinekinase (CPK), alkaline phosphatase, aspartate aminotransferace (AST), alanine aminotransferace (ALT), acid phosphatase, glucose-6-phosphate dehydrogenase and so on.

In one embodiment of the invention at least one of said two binders is bound to a solid phase as magnetic particles, and polystyrene surfaces.

The threshold for determining the risk of a subject for developing new-onset obesity is above 60 pmol/L pro-NT, preferred above 90 pmol/L, more preferred above 123 pmol/L. In a specific embodiment said threshold is above 180 pmol/L or above 190 pmol/L. These thresholds are related to the above mentioned calibration method. A pro-NT value above said threshold means that the subject has an enhanced risk of developing new-onset obesity.

Obesity is defined as a body mass index of ≥30 kg/m$^2$.

A non-obese subject is defined with a body mass index of <30 kg/m$^2$.

New-onset obesity is defined as obesity development of non-obese subjects after a certain follow-up time.

Body mass index (BMI) was defined as body weight in kilograms divided by the square of height in meters.

The time for follow-up is up to 1 year, preferably up to 2 years, more preferably up to 5 years, even more preferred more than 10 years, even more preferred up to 15 years, even more preferred up to 16.5 years, most preferred up to 18 years.

The definition of diabetes is as follows: a history of physician diagnosis or being on anti-diabetic medication or having a fasting whole blood glucose >/=6.1 mmol/l (which corresponds to >/=7.0 mmol/l in plasma) at the baseline examination.

Pre-diabetes or impaired fasting glucose (IFG) is defined as whole blood fasting plasma glucose between >/=5.4 and <6.1 mmol/l (which corresponds to 6.1-6.9 mmol/l in plasma).

In a specific embodiment of the method according to the invention said subject is a non-diabetic subject with fasting whole blood glucose of less than 5.4 mmol/l (which corresponds to <6.1 mmol/l in plasma). The metabolic syndrome was defined by the World Health Organization criteria (Alberti and Zimmet. 1998. *Diabet Med.* 15:539-553; World Health Organization. 1999. Definition, diagnosis and classification of diabetes mellitus and its complications: report of a WHO Consultation. Part 1: diagnosis and classification of diabetes mellitus. Geneva, Switzerland: World Health Organization) that require the presence of insulin resistance identified by one of the following: (1) type II diabetes; (2) impaired fasting glucose; (3) impaired glucose tolerance or (4) for those with normal fasting glucose levels (<110 mg/dL), glucose uptake below the lowest quartile for background population under investigation under hyperinsulemic, euglycemic conditions, AND two of the following:

(1) blood pressure: ≥140/90 mmHg; (2) dyslipidemia: triglycerides (TG): ≥1.695 mmol/L and high-density lipoprotein cholesterol (HDL-C) ≤0.9 mmol/L (male), ≤1.0 mmol/L (female); (3) central obesity: waist:hip ratio >0.90 (male); >0.85 (female), or body mass index >30 kg/m$^2$; (4) microalbuminuria: urinary albumin excretion ratio ≥20 µg/min or albumin:creatinine ratio ≥30 mg/g.

The subject may have normal blood pressure (BP normal blood pressure (BP). Said subject may be normotensive/high blood pressure.

The definition of normotensive/high blood pressure (HBP) is as follows:

HBP: Systolic BP>/=140 mmHg or Diastolic BP>/=90 mmHg or being on antihypertensive medications. Subjects having normal blood pressure (BP) are all other subjects, i.e subjects with systolic BP<140 mmHg or Diastolic BP<90 mmHg or not being on antihypertensive medications.

In a specific embodiment of the method according to the invention the prediction of the risk of the subject for developing new-onset obesity is improved by additionally determining and using the level of at least one laboratory parameter or further marker selected from the group comprising fasting whole blood or plasma glucose, triglycerides, HDL cholesterol or subfractions thereof, LDL cholesterol or subfractions thereof, cystatin C, insulin, CRP, estimated glomerular filtration rate (eGFR).

In a specific embodiment of the method according to the invention additionally at least one clinical parameter is determined selected from the group comprising age, gender, systolic blood pressure, diastolic blood pressure, antihypertensive treatment (AHT), waist circumference, waist-hip-ratio, current smoker, diabetes heredity, cancer heredity and previous cardiovascular disease (CVD).

A further embodiment of the invention is a method for determining the fat processing activity and/or predicting the risk of new-onset obesity, wherein the level of pro-neurotensin or fragments thereof either alone or in conjunction with other prognostically useful laboratory or clinical parameters is used for the determination of fat processing activity and/or the prediction of the risk of new-onset obesity in a subject by a method which may be selected from the following alternatives:
  comparison with the median of the level of pro-neurotensin or fragments thereof or pro-neurotensin 1-117 comprising peptides in an ensemble of pre-determined samples in a population of apparently healthy subjects,
  comparison with a quantile of the level of pro-neurotensin or fragments thereof or pro-neurotensin 1-117 comprising peptides in an ensemble of pre-determined samples in a population of apparently healthy subjects,
  calculation based on Cox Proportional Hazards analysis or by using Risk index calculations such as the NRI (Net Reclassification Index) or the IDI (Integrated Discrimination Index).

In one embodiment of the invention the sample is selected from the group comprising blood sample, a serum sample, a plasma sample, a cerebrospinal fluid sample, a saliva sample and a urine sample or an extract of any of the aforementioned samples. In a specific embodiment of the method according to the invention the level of pro-neurotensin or fragments thereof or pro-neurotensin 1-117 comprising peptide having at least a length of 5 amino acids is determined by a diagnostic assay, preferably by an immunoassay.

In a specific embodiment of the method according to the invention the method is performed more than once in order to monitor the risk of getting new-onset obesity or in order to monitor the course of treatment of said subject to reduce the risk of getting new-onset obesity in a subject wherein said subject is non-obese.

In a specific embodiment of the method according to the invention said monitoring is performed in order to evaluate the response of said subject to preventive and/or therapeutic measures taken.

In a specific embodiment of the method according to the invention the method is used in order to stratify said subjects into risk groups.

Also encompassed by the present invention is a point-of-care device for performing a method according to the invention.

Also encompassed by the present invention is an assay and/or kit for performing a method according to the invention.

EXAMPLES

Example 1

Development of Antibodies
Peptides/Conjugates for Immunization:
Peptides for immunization were synthesized (JPT Technologies, Berlin, Germany) with an additional N-terminal Cysteine residue for conjugation of the peptides to Bovine Serum Albumin (BSA). The peptides were covalently linked to BSA by using Sulfo-SMCC (Perbio-Science, Bonn, Germany). The coupling procedure was performed according to the manual of Perbio.

```
Labelled antibody (LA) peptide (P-NT 1-19):
H-CSDSEEEMKALEADFLTNMH-NH2

Solid phase antibody (SPA) peptide (P-NT 44-62):
H-CNLNSPAEETGEVHEEELVA-NH2
```

The antibodies were generated according to the following method:

A BALB/c mouse were immunized with 100 µg Peptide-BSA-Conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitoneal and one intravenous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium (RPMI 1640 culture medium supplemented with 20% fetal calf serum and HAT-Supplement). After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined. (Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Monoclonal Antibody Production

Antibodies were produced via standard antibody production methods (Marx et al, Monoclonal Antibody Production, ATLA 25, 121, 1997,) and purified via Protein A-chromatography. The antibody purities were >95% based on SDS gel electrophoresis analysis.

Example 2

Immunoassay for the Quantification of Human Pro-Neurotensin

The technology used was a sandwich coated tube luminescence immunoassay, based on Akridinium ester labelling.

Labelled compound (tracer): 100 µg (1000) LA (1 mg/ml in PBS, pH 7.4, was mixed with 10 µl Akridinium NHS-ester (1 mg/ml in acetonitrile, InVent GmbH, Germany) (EP 0353971) and incubated for 20 min at room temperature. Labelled LA was purified by Gel-filtration HPLC on Bio-Sil SEC 400-5 (Bio-Rad Laboratories, Inc., USA) The purified LA was diluted in (300 mmol/l potassiumphosphate, 100 mmol/l NaCl, 10 mmol/l Na-EDTA, 5 g/l Bovine Serum Albumin, pH 7.0). The final concentration was approx. 800.000 relative light units (RLU) of labelled compound (approx. 20 ng labeled antibody) per 200 µl. Acridiniumester chemiluminescence was measured by using an AutoLumat LB 953 (Berthold Technologies GmbH & Co. KG).

Solid phase: Polystyrene tubes (Greiner Bio-One International AG, Austria) were coated (18 h at room temperature) with SPA (1.5 µg SPA/0.3 ml 100 mmol/l NaCl, 50 mmol/l TRIS/HCl, pH 7.8). After blocking with 5% bovine serum albumine, the tubes were washed with PBS, pH 7.4 and vacuum dried.

Calibration:

The assay was calibrated, using dilutions of pro-NT-containing human serum. A pool of human sera with high pro-NT-immunoreactivity (InVent Diagostika, Hennigsdorf, Germany) was diluted with horse serum (Biochrom AG, Deutschland) (assay standards).

The standards were calibrated by use of the human pro-NT-calibrator (ICI-Diagnostics, Berlin, Germany). Alternatively, the assay may be calibrated by synthetic or recombinant pro-NT 1-117 or fragments thereof (see also Ernst et al., 2006).

Pro-NT Immunoassay:

50 µl of sample (or calibrator) was pipetted into SPA coated tubes, after adding labelled LA (2000), the tubes were incubated for 16-22 h at 18-25° C. Unbound tracer was removed by washing 5 times (each 1 ml) with washing solution (20 mM PBS, pH 7.4, 0.1% Triton X-100).

Tube-bound LA was measured by using the AutoLumat LB 953.

FIG. 1 shows a typical P-NT dose/signal curve.

Example 3

Population Study

The Malmö Diet and Cancer (MDC) study is a population-based, prospective epidemiologic cohort of 28,449 men (born 1923-1945) and women (born 1923-1950) from the city of Malmö in southern Sweden who underwent baseline examinations between 1991 and 1996 (Minisymposium: The Malmo Diet and Cancer Study. Design, biological bank and biomarker programme. J Intern Med 233, 39-79 (1993). From this cohort, 6,103 persons were randomly selected to participate in the MDC Cardiovascular Cohort (MDC-CC), which was designed to investigate the epidemiology of carotid artery disease, between 1991 and 1994 (Persson et al. 2008. Atherosclerosis 200: 191-198). Fasted plasma samples at the baseline examination were available for analysis of pro-neurotensin (pro-NT) and successfully measured in a total of 4,632 participants in the MDC-CC. Of those, complete data was available for BMI in 4,626, for waist circumference on 4,625 and for estimated degree of insulin resistance using the homeostasis model assessment of insulin resistance (HOMA-IR) (fasting blood glucose concentration×fasting plasma insulin concentration/22.5) (Matthews et al. 1985. Diabetologia 28: 412-419) in 4,468 participants. BMI was defined as body weight in kilograms divided by the square of height in meters and obesity as a BMI ≥30 kg/m². Abdominal obesity was defined as a waist circumference of ≥94 cm in males and ≥80 cm in females, according to the International Diabetes Federation definition (Alberti et al. 2006. Diabet Med 23: 469-489). Insulin resistance was regarded present in subjects belonging to the top 25% of HOMA-IR values in the MDC-CC. 'New-Onset Obesity' is defined as obesity development among non-obese MDC-CC participants who were re-examined and diagnosed with obesity after an average follow-up time of 16.5±1.5 years.

Pro-NT was measured in stored fasting plasma specimens that were frozen to −80° C. immediately at the MDC-CC baseline exam using a recent chemiluminometric sandwich immunoassay to detect a pro-NT precursor fragment (pro-NT 1-117) as described previously (Ernst et al. 2006. Peptides 27: 1787-1793). Analyses of blood glucose and plasma insulin were carried out at the time of baseline examination at the Department of Clinical Chemistry, Malmö University Hospital, which is attached to a national standardization and quality control system (Enhorning et al. 2010. Circulation 121: 2102-2108). Of the 4,626 subjects with baseline data on BMI and pro-NT, 2,900 subjects were re-examined with a new measurement of BMI after a mean follow-up of 16.5±1.5 years. In analyses of incident obesity, we excluded subjects who were obese already at the baseline examination, leaving a total of 2,606 non-obese subjects for analysis of pro-NT in relation to incident obesity. All participants gave written informed consent and the study was approved by the Ethical Committee at Lund University, Lund, Sweden.

Statistical Analyses

All subjects at the MDC-CC baseline examination were divided into ascending quartiles according to their value of fasting pro-NT. In cross sectional analyses we related baseline quartile of pro-NT to the dichotomous outcome of obesity, abdominal obesity and insulin resistance using age and sex adjusted logistic regression models. In the analyses of incident obesity, we related baseline quartile of pro-NT to the dichotomous outcome of incident obesity using logistic regression adjusted for baseline age, sex and BMI. Data are presented as odds ratios (95% confidence intervals) and subjects belonging to the lowest quartile of pro-NT were defined as the referent group (odds ratio=1). 'P for trend' denotes the P-value for linear trend over quartiles 1-4.

Study Results

We measured pro-NT levels in fasted plasma of 4,632 middle-aged subjects of the population-based Malmö Diet and Cancer Study Cardiovascular Cohort (Table 1). The age- and sex-adjusted likelihood of being obese, abdominally obese and insulin resistant significantly increased across quartiles of pro-NT (Table 2). Among non-obese subjects, the risk of developing obesity during an average follow-up time of 16.5±1.5 years increased gradually with pro-NT quartiles, independently of baseline body mass index, age and gender. Pro-NT median concentrations were 60.1 pmol/L (range 3.3-75.9 pmol/L) in quartile 1, 89.3 pmol/L (range 75.9-105 pmol/L) in quartile 2, 123 pmol/L (range 105-149 pmol/L) in quartile 3 and 190 pmol/L (range 149-1155 pmol/L) in quartile 4. Non-obese subjects in the top quartile of baseline pro-NT levels had a more than doubling (OR 2.06 (95% confidence interval of 1.38-3.06) of the risk of developing obesity as compared to subjects in the lowest quartile (Table 2).

Using the same variables in the equation, we investigated different subgroups for prediction of new-onset obesity (Table 3), subjects with diabetes mellitus (DM) and impaired fasting glucose (IFG), high blood pressure/anti-hypertensive therapy (AHT), metabolic syndrome (MeSy), eGFR <60 (ml/min/1.73 $m^2$), heredity of cancer, prevalent cancer, smokers, respectively, at baseline were excluded. Non-obese subjects in the highest pro-NT level quartile either none of the above mentioned conditions again showed a more than doubling of the risk of developing obesity compared to subjects in the lowest pro-NT quartile (Table 3). Non-obese subjects with none of these conditions (super healthy subjects) in the highest pro-NT level quartile even showed a more than 3 fold increased risk of developing obesity compared to subjects in the lowest pro-NT quartile.

Example 4

PNT Concentrations Before and after an Oral Fat Up-Take Test ("Cream-Test")

A total of 54 patients, 19 healthy control subjects and 35 patients with a diagnosis of heart failure, were selected. The subjects fasted for at least 10 hours and ingested a standardized fat-enriched drinking solution (cream containing 30% of fat). Blood was taken at baseline and 1, 2 and 3 hours after cream up-take. Pro-Neurotensin was measured with the immunoassay as described above. Baseline pro-NT was defined as 100% and levels at the three different time points were related thereto. Pro-NT significantly increased 1 hour after cream intake in both, healthy controls and patients with HF and decreased after 2 and 3 hours but without reaching the baseline level (FIG. 2). Moreover, the relative concentration of pro-NT was significantly different between healthy controls and patients with HF at all three time points (p<0.05).

TABLE 1

Clinical characteristics of the Malmo Diet and Cancer Cardiovascular Cohort (MDC-CC)

| Characteristic | Value | N |
| --- | --- | --- |
| Age (years) | 57.7 ± 6.0 | 4,626 |
| Female sex, n (%) | 2661 (57.5) | 4,626 |
| Body Mass Index (kg/$m^2$) | 25.8 ± 3.9 | 4,626 |
| Waist circumference (cm) | 84.0 ± 12.9 | 4,625 |
| Fasting blood glucose (mM) | 5.2 ± 1.4 | 4,468 |
| Fasting insulin concentration (mU/L) | 7.0 (4.0-9.0) | 4,468 |
| HOMA-IR | 1.5 (0.9-2.2) | 4,468 |

Data are given as mean±standard deviation for normally distributed variables, and as median and interquartile range for fasting insulin concentration. Categorical data are presented as numbers (percentages). "N" denotes the number with complete data; thus, included in analyses. "HOMA-IR" stands for Homeostasis Model Assessment of Insulin Resistance (fasting plasma insulin concentration×fasting blood glucose concentration/22.5)

TABLE 2

Fasting plasma concentration of pro-neurotensin (pro-NT) in relation to prevalence of obesity and insulin resistance and in relation to incidence of new-onset obesity during long term follow-up in the Malmö Diet and Cancer Cardiovascular Cohort

| | N/N cases | Odds ratio (95% confidence interval) | | | | P for trend |
| --- | --- | --- | --- | --- | --- | --- |
| | | Pro-NT Quartile 1 | Pro-NT Quartile 2 | Pro-NT Quartile 3 | Pro-NT Quartile 4 | |
| Prevalent obesity | 4626/604 | 1.0 (ref) | 1.00 (0.78-1.29) | 1.13 (0.88-1.45) | 1.34 (1.05-1.70) | 0.01 |
| Prevalent abdominal obesity | 4625/1769 | 1.0 (ref) | 1.07 (0.90-1.27) | 1.23 (1.04-1.46) | 1.30 (1.09-1.54) | 0.001 |
| Prevalent insulin resistance | 4468/1140 | 1.0 (ref) | 1.30 (1.06-1.59) | 1.43 (1.17-1.74) | 1.70 (1.39-2.06) | <0.0001 |
| New-onset obesity | 2606/335 | 1.0 (ref) | 1.44 (0.95-2.10) | 1.83 (1.21-2.65) | 2.06 (1.38-3.06) | <0.01 |

'N/N cases' denotes 'total number of subjects in the analysis/number of cases with the disease in question.' 'Pro-NT' denotes fasting plasma concentration of pro-neurotensin at the MDC-CC baseline examination. 'Pro-NT Quartiles 1-4' defines the MDC-CC population quartiles (lowest to highest) of pro-NT. Data are presented as odds ratios (95% confidence intervals) and subjects belonging to the lowest quartile of pro-NT were defined as the referent group (odds ratio=1). 'P for trend' denotes the P-value for linear trend over quartiles 1-4. Prevalent means that the subjects already had the 'disease in question' at baseline, whereas the subjects with prevalent obesity where excluded in the analysis for risk-prediction of new onset obesity.

TABLE 3

Fasting plasma concentration of pro-neurotensin (pro-NT) in relation to incidence of new-onset obesity in different subgroups of patients during long term follow-up in the Malmö Diet and Cancer Cardiovascular Cohort

| | N/N cases | Pro-NT Quartile 1 | Pro-NT Quartile 2 | Pro-NT Quartile 3 | Pro-NT Quartile 4 | P for trend |
|---|---|---|---|---|---|---|
| all | 2606/335 | 1.0 (ref) | 1.44 (0.95-2.10) | 1.83 (1.21-2.65) | 2.06 (1.38-3.06) | <0.01 |
| Male | 1080/137 | 1.0 (ref) | 1.43 (0.79-2.59) | 1.36 (0.75-2.48) | 2.36 (1.29-4.30) | 0.044 |
| Female | 1526/198 | 1.0 (ref) | 1.45 (0.85-2.46) | 2.23 (1.32-3.75) | 1.88 (1.09-3.21) | 0.019 |
| No hereditary cancer | 1456/197 | 1.0 (ref) | 1.65 (0.99-2.77) | 1.68 (0.99-2.85) | 2.37 (1.41-3.97) | 0.014 |
| No prevalent cancer | 2362/301 | 1.0 (ref) | 1.36 (0.89-2.06) | 1.96 (1.29-2.95) | 2.1 (1.38-3.19) | 0.001 |
| BP <140 | 1631/197 | 1.0 (ref) | 1.29 (0.77-2.18) | 1.88 (1.13-3.15) | 2.03 (1.21-3.39) | 0.023 |
| No AHT | 2269/273 | 1.0 (ref) | 1.63 (1.05-2.53) | 2.03 (1.31-3.13) | 2.12 (1.35-3.35) | 0.004 |
| BP <140/no AHT | 1526/175 | 1.0 (ref) | 1.44 (0.83-2.49) | 1.99 (1.15-3.42) | 2.16 (1.24-3.73) | 0.026 |
| Non-smoker | 2001/241 | 1.0 (ref) | 1.47 (0.93-2.32) | 1.75 (1.12-2.74) | 2.26 (1.42-3.61) | 0.006 |
| No prevalent cardiac disease | 2544/326 | 1.0 (ref) | 1.51 (1.00-2.26) | 1.95 (1.30-2.90) | 2.17 (1.44-3.26) | 0.001 |
| eGFR >60 | 2319/320 | 1.0 (ref) | 1.36 (0.90-2.04) | 1.77 (1.18-2.64) | 2.22 (1.47-3.35) | 0.001 |
| No IFG or DM | 2152/254 | 1.0 (ref) | 1.44 (0.91-2.28) | 2.03 (1.30-3.19) | 2.46 (1.55-3.90) | <0.001 |
| No MeSy | 2426/302 | 1.0 (ref) | 1.44 (0.96-2.18) | 1.92 (1.28-2.89) | 2.03 (1.34-3.07) | 0.003 |
| Healthy all | 1155/123 | 1.0 (ref) | 1.84 (0.95-3.57) | 2.68 (1.41-5.09) | 3.17 (1.57-6.37) | 0.005 |
| Healthy Female | 681/74 | 1.0 (ref) | 1.35 (0.56-3.25) | 2.96 (1.28-6.86) | 3.46 (1.37-8.73) | 0.015 |

'N/N cases' denotes 'total number of subjects in the analysis/number of cases with the disease in question.' 'Pro-NT' denotes fasting plasma concentration of pro-neurotensin at the MDC-CC baseline examination. 'Pro-NT Quartiles 1-4' defines the MDC-CC population quartiles (lowest to highest) of pro-NT. Data are presented as odds ratios (95% confidence intervals) and subjects belonging to the lowest quartile of pro-NT were defined as the referent group (odds ratio=1). 'P for trend' denotes the P-value for linear trend over quartiles 1-4.

Heredity of cancer means no known cancer in family history at baseline, no prevalent cancer means no diagnosis of cancer at baseline, no prevalent cardiac disease means no myocardial infarction, ischemic heart disease, stroke, heart failure (acute or chronic heart failure), atrial fibrillation and atrial flutter at baseline, BP=blood pressure, AHT=antihypertensive therapy, eGFR=estimated glomerular filtration rate, IFG=impaired fasting glucose, DM=diabetes mellitus, MeSy=metabolic syndrome.

TABLE 4

Pro-Neurotensin concentration at baseline (fasting) and 1, 2 and 3 hours after cream intake in healthy control subjects and subjects with heart failure (HF)

| | pro-NT [in %] | | | |
|---|---|---|---|---|
| | baseline | 1 h | 2 h | 3 h |
| control | 100 | 173.5 | 147.0 | 133.0 |
| HF | 100 | 227.5 | 201.8 | 179.3 |

PNT values are given in % related to the baseline value, which was defined for both groups as 100%, respectively.

The invention claimed is:

1. A method for determining fat processing activity and/or for predicting risk of obesity in a subject comprising:
   determining by an immunoassay a level of pro-neurotensin 1-117 (SEQ ID NO: 5) or a level of peptides that comprise the amino acid sequence of pro-neurotensin 1-117 (SEQ ID NO: 5) in a sample of bodily fluid obtained from said subject;
   correlating said level of pro-neurotensin 1-117 (SEQ ID NO: 5) or said level of peptides that comprise the amino acid sequence of pro-neurotensin 1-117 (SEQ ID NO: 5) with fat processing activity and/or a risk of incidence of obesity in said subject, wherein a level above a threshold level is indicative of an enhanced fat processing activity and/or predictive for an enhanced risk of obesity, and
   reducing said subject's fat uptake if said level of pro-neurotensin 1-117 (SEQ ID NO: 5) or said level of peptides that comprise the amino acid sequence of pro-neurotensin 1-117 (SEQ ID NO: 5) is above said threshold level,
   wherein said subject is not obese when said sample of bodily fluid is taken from said subject,
   wherein the subject does not have metabolic syndrome, and
   wherein said immunoassay comprises (i) contacting said sample with one or more antibodies, at least one of which is labelled, that specifically bind to an epitope within pro-neurotensin 1-117 (SEQ ID NO: 5), to form a complex between the antibody and pro-neurotensin 1-117 (SEQ ID NO: 5) or peptides that comprise the amino acid sequence of pro-neurotensin 1-117 (SEQ ID NO: 5), and (ii) quantitating the level of the thus-formed complex.

2. A method according to claim 1, wherein said subject is a non-prediabetic subject.

3. A method according to claim 1, wherein a fasting level of pro-neurotensin 1-117 (SEQ ID NO: 5) or of peptides that comprise the amino acid sequence of pro-neurotensin 1-117 (SEQ ID NO: 5) is determined.

4. A method according to claim 1, wherein the level of pro-neurotensin 1-117 (SEQ ID NO: 5) is determined.

5. A method according to claim 1 wherein the subject is non-diabetic with fasting whole blood glucose of less than 6.1 mmol/l but more than 5.4 mmol/l.

6. A method according to claim 1 wherein the subject does not have cancer.

7. A method according to claim 1 wherein the subject has no history of diagnosis of an acute cardiovascular event when said sample of bodily fluid is taken from said subject wherein said cardiovascular event is selected from myocardial infarction, stroke, and acute heart failure.

8. A method according to claim 1, wherein said subject is a subject with fasting whole blood glucose of less than 5.4 mmol/1.

9. A method according to claim 1, wherein the risk of obesity is independent of a risk for contracting diabetes mellitus and/or metabolic syndrome.

10. A method according to claim 1, wherein additionally at least one clinical parameter is determined in the subject selected from age, gender, systolic blood pressure, diastolic blood pressure, antihypertensive treatment (AHT), waist circumference, waist-hip-ratio, current smoker, diabetes heredity and previous cardiovascular disease (CVD).

11. The method according to claim 1, wherein the sample is selected from a blood sample, a serum sample, a plasma sample, a cerebrospinal fluid sample, a saliva sample and a urine sample or an extract of any of the aforementioned samples.

12. A method according to claim 1, wherein said method is performed more than once in order to monitor the risk of incidence of obesity.

13. A method according to claim 12, wherein said monitoring is performed in order to evaluate a response of said subject to preventive and/or therapeutic measures taken.

14. A method according to claim 1, wherein said method is performed in a plurality of subjects in order to stratify said subjects into risk groups.

15. A method according to claim 1, wherein said threshold level is at least 60 pmol/L pro-neurotensin 1-117 (SEQ ID NO: 5).

16. A method according to claim 1, wherein said threshold level is at least 90 pmol/L pro-neurotensin 1-117 (SEQ ID NO: 5).

17. A method according to claim 1, wherein said threshold level is at least 123 pmol/L pro-neurotensin 1-117 (SEQ ID NO: 5).

18. A method according to claim 1, wherein said threshold level is at least 180 pmol/L pro-neurotensin 1-117 (SEQ ID NO: 5).

19. A method according to claim 1, wherein peptides that comprise the amino acid sequence of pro-neurotensin 1-117 (SEQ ID NO: 5) are selected from peptides of SEQ ID NO: 1, SEQ ID NO: 2, SEQ ID NO: 6, and SEQ ID NO: 7.

20. A method for determining fat processing activity and/or for predicting risk of obesity in a subject comprising:
- determining by an immunoassay a level of pro-neurotensin 1-117 (SEQ ID NO: 5) or a level of peptides that comprise the amino acid sequence of pro-neurotensin 1-117 (SEQ ID NO: 5) in a non-fasting or fasting sample of bodily fluid obtained from said subject,
- administering fat to said subject,
- determining by an immunoassay a level of pro-neurotensin 1-117 (SEQ ID NO: 5) or a level of peptides that comprise the amino acid sequence of pro-neurotensin 1-117 (SEQ ID NO: 5) in a sample of bodily fluid obtained from said subject after fat-uptake,
- calculating a difference between said levels after and before fat-uptake,
- correlating said difference between said levels after and before fat-uptake of pro-neurotensin 1-117 (SEQ ID NO: 5) or of said peptides that comprise the amino acid sequence of pro-neurotensin 1-117 (SEQ ID NO: 5) with fat processing activity and/or a risk of incidence of obesity in said subject, wherein a higher difference is more indicative of an enhanced fat processing activity and/or more predictive of an enhanced risk of obesity than a lower difference, and
- reducing said subject's fat uptake if said higher difference is calculated;
- wherein the subject is not obese when the samples of bodily fluid are taken from said subject, and wherein said immunoassay comprises (i) contacting said sample with one or more antibodies, at least one of which is labelled, that specifically bind to an epitope within pro-neurotensin 1-117 (SEQ ID NO: 5), to form a complex between the antibody and pro-neurotensin 1-117 (SEQ ID NO: 5) or peptides that comprise the amino acid sequence of pro-neurotensin 1-117 (SEQ ID NO: 5), and (ii) quantitating the level of the thus-formed complex.

* * * * *

SEQUENCE LISTING

<160> NUMBER OF SEQ ID NOS: 12

Figure 1:
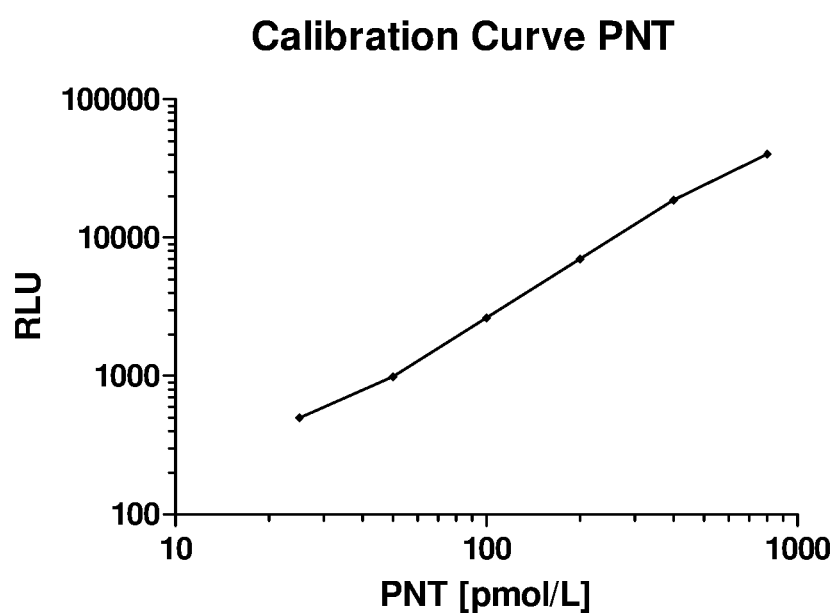
FIG. 1 shows a typical P-NT dose/signal curve.
Figure 2:
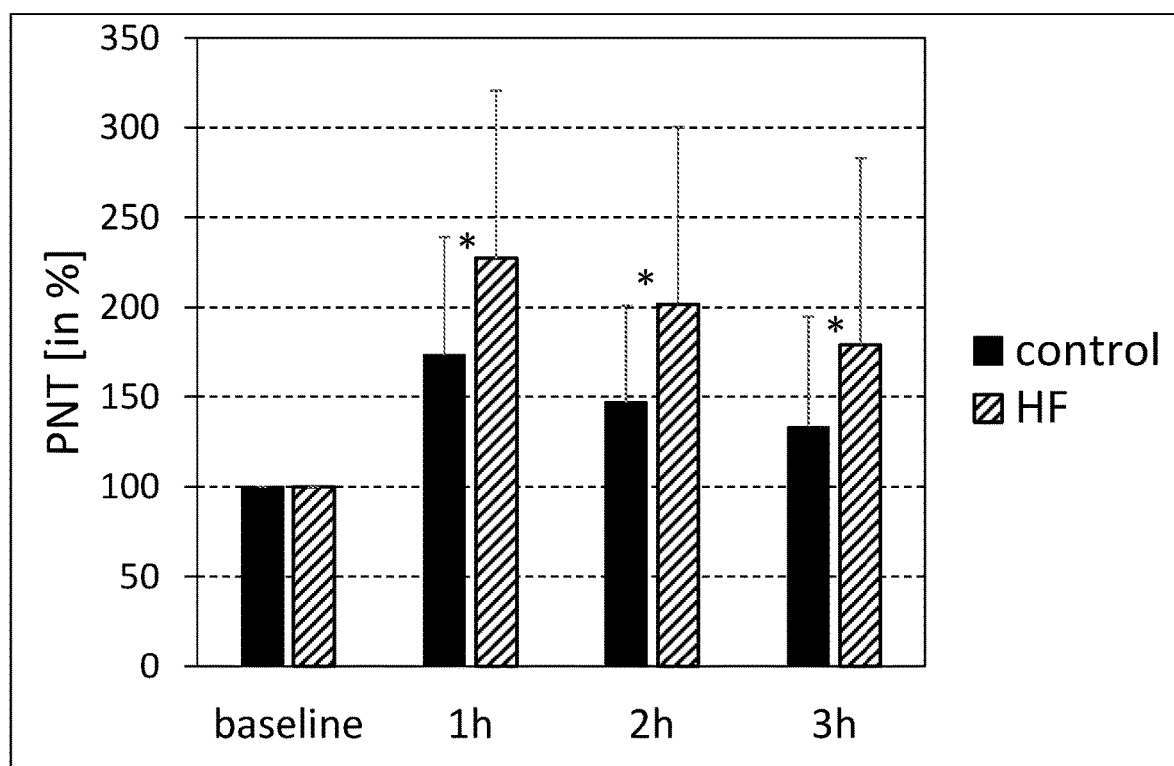
FIG. 2 shows PNT level before and after cream up-take in patients with heart failure and a control group.

<210> SEQ ID NO 1
<211> LENGTH: 147
<212> TYPE: PRT
<213> ORGANISM: Homo sapiens

<400> SEQUENCE: 1

```
Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
                100                 105                 110

Lys Glu Glu Val Ile Lys Arg Lys Ile Pro Tyr Ile Leu Lys Arg Gln
                115                 120                 125

Leu Tyr Gln Asn Lys Pro Arg Arg Pro Tyr Ile Leu Lys Arg Asp Ser
    130                 135                 140

Tyr Tyr Tyr
145

<210> SEQ ID NO 2
<211> LENGTH: 125
<212> TYPE: PRT
<213> ORGANISM: Homo sapiens

<400> SEQUENCE: 2

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
                100                 105                 110

Lys Glu Glu Val Ile Lys Arg Lys Ile Pro Tyr Ile Leu
                115                 120                 125

<210> SEQ ID NO 3
<211> LENGTH: 6
<212> TYPE: PRT
<213> ORGANISM: Homo sapiens

<400> SEQUENCE: 3

Lys Ile Pro Tyr Ile Leu
1               5

<210> SEQ ID NO 4
<211> LENGTH: 13
<212> TYPE: PRT
<213> ORGANISM: Homo sapiens
```

<400> SEQUENCE: 4

Gln Leu Tyr Glu Asn Lys Pro Arg Arg Pro Tyr Ile Leu
1               5                   10

<210> SEQ ID NO 5
<211> LENGTH: 117
<212> TYPE: PRT
<213> ORGANISM: Homo sapiens

<400> SEQUENCE: 5

Ser Asp Ser Glu Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile
        115

<210> SEQ ID NO 6
<211> LENGTH: 132
<212> TYPE: PRT
<213> ORGANISM: Homo sapiens

<400> SEQUENCE: 6

Ser Asp Ser Glu Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu Lys Arg Gln
        115                 120                 125

Leu Tyr Glu Asn
    130

<210> SEQ ID NO 7
<211> LENGTH: 140
<212> TYPE: PRT
<213> ORGANISM: Homo sapiens

<400> SEQUENCE: 7

-continued

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
        50                  55                  60

Lys Leu Pro Thr Ala Leu Asp Gly Phe Ser Leu Gly Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu Lys Arg Gln
            115                 120                 125

Leu Tyr Glu Asn Lys Pro Arg Arg Pro Tyr Ile Leu
        130                 135                 140

<210> SEQ ID NO 8
<211> LENGTH: 21
<212> TYPE: PRT
<213> ORGANISM: Homo sapiens

<400> SEQUENCE: 8

Lys Ile Pro Tyr Ile Leu Lys Arg Gln Leu Tyr Glu Asn Lys Pro Arg
1               5                   10                  15

Arg Pro Tyr Ile Leu
            20

<210> SEQ ID NO 9
<211> LENGTH: 28
<212> TYPE: PRT
<213> ORGANISM: Homo sapiens

<400> SEQUENCE: 9

Lys Ile Pro Tyr Ile Leu Lys Arg Gln Leu Tyr Glu Asn Lys Pro Arg
1               5                   10                  15

Arg Pro Tyr Ile Leu Lys Arg Asp Ser Tyr Tyr Tyr
            20                  25

<210> SEQ ID NO 10
<211> LENGTH: 20
<212> TYPE: PRT
<213> ORGANISM: Homo sapiens

<400> SEQUENCE: 10

Gln Leu Tyr Glu Asn Lys Pro Arg Arg Pro Tyr Ile Leu Lys Arg Asp
1               5                   10                  15

Ser Tyr Tyr Tyr
            20

<210> SEQ ID NO 11
<211> LENGTH: 23
<212> TYPE: PRT
<213> ORGANISM: Homo sapiens

<400> SEQUENCE: 11

His Cys Ser Asp Ser Glu Glu Glu Met Lys Ala Leu Glu Ala Asp Phe

```
                1               5                   10                  15
Leu Thr Asn Met His Asn His
                20

<210> SEQ ID NO 12
<211> LENGTH: 23
<212> TYPE: PRT
<213> ORGANISM: Homo sapiens

<400> SEQUENCE: 12

His Cys Asn Leu Asn Ser Pro Ala Glu Glu Thr Gly Glu Val His Glu
1               5                   10                  15

Glu Glu Leu Val Ala Asn His
                20
```